(12) United States Patent
Cheng et al.

(10) Patent No.: US 8,481,094 B2
(45) Date of Patent: Jul. 9, 2013

(54) USE OF SILYMARIN AND SILYBIN IN THE TREATMENT OF NEURAL INJURY

(75) Inventors: Henrich Cheng, Taipei (TW); May-Jywan Tsai, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 302 days.

(21) Appl. No.: 12/754,305

(22) Filed: Apr. 5, 2010

(65) Prior Publication Data

US 2011/0021614 A1    Jan. 27, 2011

Related U.S. Application Data

(60) Provisional application No. 61/228,434, filed on Jul. 24, 2009.

(51) Int. Cl.
*A61K 36/00* (2006.01)

(52) U.S. Cl.
USPC .......................................... 424/776

(58) Field of Classification Search
USPC .......................................... 424/776
See application file for complete search history.

(56) References Cited

U.S. PATENT DOCUMENTS

| 2006/0008543 | A1 | 1/2006 | Myhill et al. | |
| 2010/0166796 | A1* | 7/2010 | Keller et al. | 424/195.15 |

FOREIGN PATENT DOCUMENTS

| WO | 2008/095093 | 8/2008 |
| WO | 2010/036961 | 4/2010 |

OTHER PUBLICATIONS

Wilkinson GR, Chapter 1 Pharmacokinetics—The Dynamics of Drug Absorption, Distribution, and Elimination, "Goodman & Gilman's The Pharmacological Basis of Therapeutics, 10th ed." Hardman JG, Limbird LE, and Gilman AG, Eds., McGraw-Hill, 2001, 3-30 (pp. 3 and 5-8 provided).*
Jimenez Hamann MC, Tsai EC, Tator CH, Shoichet MS. Novel intrathecal delivery system for treatment of spinal cord injury. Exp Neurol. Aug. 2003;182(2):300-9.*
Toklu et al. "Silymarin, the Antioxidant Compenent of *Silybum marianum*, Prevents Sepsis-Induced Acute Lung and Brain Injury." Journal of Surgical Research 145, (2008), pp. 214-222.
Welin et al. "Effects of N-acetyl-cysteine on the survival and regeneration of sural sensory neurons in adult rats." Brain Research, Science Direct 2009, pp. 58-66.
Min et al. "Immunosuppressive Effect of Silibinin in Experimental Autoimmune Encephalomyelitis." Archives of Pharmacal Research, vol. 30, No. 10, 2007. pages 1265-1272.
Juurlink et al. "Review of Oxidative Stress in Brain and Spinal Cord Injury." Journal of Spinal Cord Medicine, vol. 21, No. 4, Oct. 1998, pp. 309-334.
Supplementary European Search Report issued in Application No. 10158019.9-1216 dated Oct. 27, 2010, 10 pages.
Tsai, et al. 2008, "Neuroprotective effect of silymarin on injured spinal cord neurons: in culture and in vivo studies," Neuroscience 2008, (Abstract only; presented on Nov. 19, 2008).

* cited by examiner

*Primary Examiner* — Paul Zarek
(74) *Attorney, Agent, or Firm* — Wolf, Greenfield & Sacks, P.C.

(57) ABSTRACT

The present invention provides a method of treating neural injury, e.g., spinal cord injury (SCI), or enhancing recovery from the neural injury with silymarin or silybin.

4 Claims, 7 Drawing Sheets

(A)

(B)

USE OF SILYMARIN AND SILYBIN IN THE TREATMENT OF NEURAL INJURY

RELATED APPLICATION

This application claims priority to U.S. Provisional Application No. 61/228,434, filed on Jul. 24, 2009, the content of which is hereby incorporated by reference in its entirety.

FIELD OF THE INVENTION

The present invention relates to use of silymarin or silybin for treating neural injury.

BACKGROUND OF THE INVENTION

Silymarin, a mixture of flavonolignans isolated from milk thistle (*Silybum marianum*), is commonly used for treating liver disorders. It also exhibits anti-inflammatory, cytoprotective, and anticarcinogenic activities. Silybin is the major flavonolignan in silymarin and has been found to possess the above-mentioned therapeutic effects.

Spinal cord injury (SCI) is damage to the spinal cord that results in loss of sensation and motor control. It can be caused by a disease (e.g., Friedreich's ataxia) or a physical trauma (e.g., contusion) on the spinal cord.

BRIEF SUMMARY OF THE INVENTION

The present invention is based on the unexpected discovery that silymarin or silybin possesses neuroprotective activity and improves functional recovery of rats suffering from spinal cord injury.

Accordingly, the present invention relates to a method for treating neural injury (e.g., SCI) by administering to a subject in need thereof an effective amount of silymarin or silybin. In particular, the silymarin or silybin can be delivered to an injured neural area. In one example, it is administered intrathecally via injection. The silybin used in the method of this invention can be in isolated form, i.e., prepared by a synthetic method or enriched from a natural source (e.g., *Silybum marianum*). An isolated silybin compound refers to a preparation that contains at least 40% of the compound by dry weight. Purity of an isolated compound can be measured by, e.g., column chromatography, mass spectrometry, high performance liquid chromatography (HPLC), NMR, or any other suitable methods.

The term "treating" as used herein refers to the application or administration of a composition including one or more active agents to a subject, who has a neural injury, a symptom of the injury, or a predisposition toward the injury, with the purpose to cure, heal, alleviate, relieve, alter, remedy, ameliorate, improve, or affect the injury, the symptoms of the injury, or the predisposition toward the injury. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents.

The present invention also relates to a method for enhancing recovery from SCI (e.g., contusive SCI) with silymarin or silybin.

Also within the scope of this invention is the use of silymarin or silybin for the manufacture of a medicament for treating a neural injury.

The details of one or more embodiments of the invention are set forth in the description below. Other features or advantages of the present invention will be apparent from the following drawings and detailed description of several embodiments, and also from the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
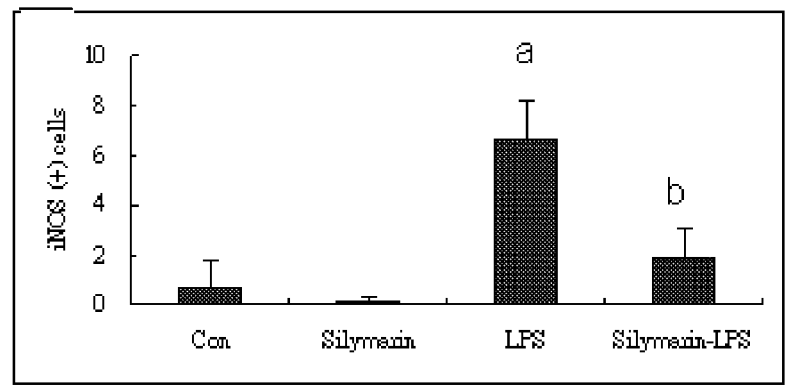
FIG. 1 shows the effect of silymarin and silybin on LPS- and kainate-induced toxicity in rat spinal cord neuronal-glial cultures wherein (A) shows the number of iNOS-positive cells per 1.5 mm$^2$ in each treatment group (Con=the control group; a: P<0.05 (LPS vs control); b: P<0.05 (LPS+SM vs LPS)) and (B) shows the amount of nitrite released into culture medium in each treatment group (a: P<0.05 (treatment vs control); b: P<0.05 (SM/LPS or SB/LPS vs LPS); SM=silymarin; SB=silybin).
Figure 1:
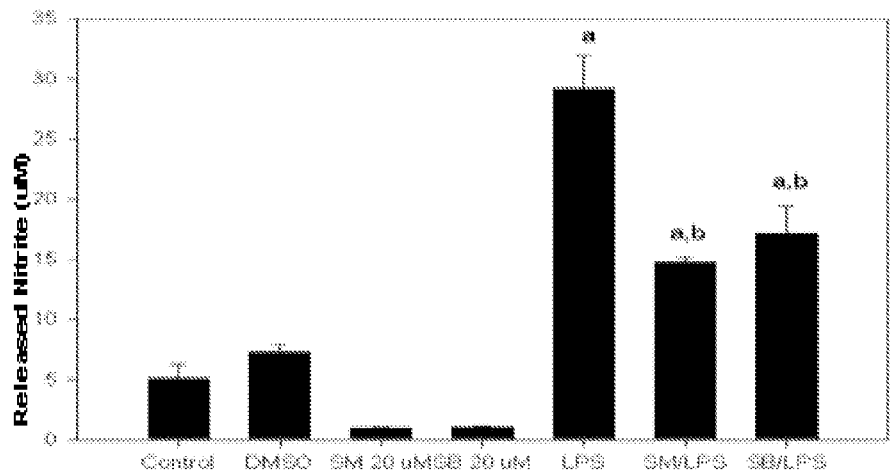

The present invention relates to the use of silymarin and silybin for treating neural injury and facilitating recovery from such injury.

When used herein, the phrase "recovery from SCI" refers to improvement in the pathological conditions of the subject suffering from SCI and/or restoration (at least partially) of the physical function of the injured spinal cord. For example, in the animal model used in the examples of the present invention, the spinal cords of rats were contusively injured in the T9-T10 area. In such case, recovery from the SCI was demonstrated by improvement in motor deficits of the hindlimbs.

Silymarin is a standardised extract from the seeds and fruits of the milk thistle *Silybum marianum* Gaertn (also known as Carduus marianus L) and contains, as its main constituents, the flavonolignans silybin (synonymous with silibinin) Silymarin may be prepared by any conventional methods, see for example, the techniques disclosed in Barreto et al. (Extraction of nutraceuticals from milk thistle. Hot water extraction; Appl. Biochem Biotechnol. 108:881-9, 2003), Wallace et al. (Extraction of nutraceuticals from milk thistle: part II. Extraction with organic solvents; Appl. Biotechnol. 105-108:891-903, 2003) and Wallace et al. (Batch solvent extraction of flavanolignans from milk thistle; Phyotchemical Analysis. 16:7-16, 2005.) Alternatively, it can be purchased from commercial vendors, such as Sigma-Aldrich (St. Louis, Mo.).

Silybin, i.e., silibinin or 2,3-dihydro-3-(4-hydroxy-3-methoxy phenyl)-2-(hydroxymethyl)-6-(3,5,7-trihydroxy-4-oxobenzopyran-2-yl)benzodioxin, has two diastereomeric forms. Both isomers can be isolated from natural sources or prepared by synthetic methods. Like silymarin, silybin is also commercially available from Sigma-Aldrich (St. Louis, Mo.) and other suppliers.

In particular, to achieve a better effect, silymarin or silybin can be administered directly to an injured neural area. In one embodiment, silymarin or silybin is administered intrathecally, i.e., injected into the cerebrospinal fluid bathing the spinal cord and brain.

To facilitate delivery, silymarin or silybin can be formulated into a pharmaceutical compositions with a suitable pharmaceutically acceptable carrier. The term "pharmaceutically acceptable carrier" as used herein refers to a carrier that is compatible with the active ingredient of the composition, and preferably, capable of stabilizing the active ingredient and not deleterious to the subject to be treated. Exemplary carriers include, but are not limited to, saline, buffered saline, dextrose, water, glycerol, ethanol and combinations thereof.

The amount of silymarin or silybin to be administered to the area of SCI varies in view of many parameters, such as the conditions of the subject and the type and severity of the SCI. The amount of silymarin or silybin, when applied to the subject suffering from SCI, should attain a desired effect, i.e., repairing injured area and/or enhancing at least partially functional recovery of the injured spinal cord. A suitable amount can be readily determined in view of the present disclosure by persons of ordinary skill in the art without undue experimentation.

The present invention is further illustrated with the following examples. These examples are offered for the purpose of illustration and are not to be construed in any way as limiting the scope of the present invention.

EXAMPLES

Chemicals

Silymarin and silybin were purchased from Sigma-Aldrich (St. Louis, Mo.) (Product Nos. 50292 and 50417, respectively). Silymarin or silibinin was dissolved in dimethyl-sulfoxide (DMSO) and freshly diluted in culture media for all in vitro culture experiments.

Liquid-chromatographic grade solvents and reagents were obtained from E. Merck (Darmstadt, Germany).

Other reagents were purchased from Sigma-Aldrich unless stated otherwise.

Mixed Neuronal/Glial Cultures

Mixed neuron-glia cell cultures were prepared from the cortical or spinal regions of embryonic Sprague-Dawley rat fetus at gestation day 15 as described in Hung et al. (*Mol. Brain Res.* 75 (2000): 330-336) and Tsai et al. (*Ann. N.Y. Acad. Sci.* 1042 (2005) :338-348). Briefly, cells were dissociated with mixtures of papain/protease/deoxyribonuclease I (0.1%: 0.1%: 0.03%) and plated onto poly-lysine coated dishes at a density of $1-2 \times 10^5$ cells/cm$^2$. Cells were maintained in Dulbecco's modified Eagle's medium (DMEM) supplemented with 10% fetal bovine serum (FBS).

Mixed Glial Cultures

Mixed glial cultures were prepared from cerebral cortex or spinal cords of newborn Spraque-Dawley rats as described in Tsai and Lee (*Free Radical Biology & Medicine* 24 (1998): 705-713). Briefly, triturated cortex or spinal cords were passed through nylon clothes (80 and 10 μm), plated in 75 cm$^2$ flasks and maintained in DMEM containing 5.5 mM glucose and supplemented with 10% fetal calf serum (FCS). The cells were incubated at 37° C. in a water-saturated atmosphere of 5% $CO_2$/95% air. To free cultures from contaminated cells, cultures were purified on the 10$^{th}$ day by shaking overnight at 180 rpm to remove the suspended cells. Cultures in the flasks were replated into multiwell plates. Cultures showed greater than 90% positive staining for glial fibrillary acidic protein (GFAP).

Microglial Cultures

Microglial cultures were purified from rat mixed glial cultures (Tzeng and Huang, *J. Cell Biochem.* 90(2) (2003): 227-33). Briefly, after 10 to 14 days in culture, floating cells and weakly attached cells on the mixed glial cell layer were isolated by shaking the flask. The resulting cell suspension was transferred to multiwell plates (Corning, USA) and allowed to adhere at 37° C. Unattached cells were removed after 30 mins, microglia were isolated as strongly adhering cells. The purity of microglia was more than 96% as determined by the immunostaining of ionized calcium-binding adapter molecule-1 (IBA1, Wako Chemicals, Japan) or ED-1(Serotec, UK).

Animals

Sprague-Dawley (SD) rats were obtained from the Animal Center of National Yang-Ming University or National Science Council, Taiwan. Female adult SD rats ranging from 240-280 g were used as inductive contusive SCI models. Animal handling and experimental protocols were carefully reviewed and approved by the animal studies committee of Taipei Veteran General Hospital.

Spinal Cord Contusion

Contusive SCI was induced using the NYU weight-drop device. Female adult SD rats were anesthetized. Dorsal laminectomy was carried out at the level of the ninth thoracic (T) vertebra. The dorsal surface of T9-T10 spinal cord was injured by dropping a 10 g rod from a height of 50 mm. The dura was left mechanically intact, while weight-drop injury led to the characteristic of egg-shaped zone of necrosis, extending several spinal cord segments rostrocaudally (Grossman et al., *Exp Neurol.* 168(2) (2001): 283-9; Widenfalk et al., *J Neurosci.* 21(10) (2001): 3457-75).

Example 1

Silymarin Does Not Affect the Cell Types in Spinal Cord Neuronal-Glial Cultures

On the second day after cell seeding, mixed neuronal/glial cultures were incubated with silymarin (40 μM) for 3 days. Cells were then processed for immunohistochemistry for neuronal, astroglial or microglial markers.

Primary neuronal-glial cultures were plated on poly-lysine coated plates and fixed in 4% paraformaldehyde solution for 20 mins. Cells were permeabilized with 0.2% Triton X-100. Cells were then stained with primary antibodies, including anti-βIII tubulin (Covance MMS-435P), anti-GFAP (Chemicon AB 5804) and anti-ED1 (Serotec MCA 341) antibodies, and with the respective fluorescently tagged secondary antibodies (Jackson ImmunoResearch Inc.). βIII tubulin is a neuron-specific marker, GFAP is an astroglial marker, and ED1 is a microglial marker. Images of spinal neurons or non-neuronal cells were obtained with a fluorescent microscope equipped with fluorescence optics. Images of neurons or immunoreactive cells were taken with a CCD camera.

According to the results (data not shown), silymarin does not affect neuronal survival and non-neuronal cell numbers in the spinal cord cultures.

Example 2

Silymarin Protects Spinal Cord Neuronal-Glial Cultures from LPS- and Kainate-Induced Toxicity On the second day after cell seeding, mixed neuronal-glial cultures were treated with silymarin (40 μM) in the presence or absence of endotoxin lipopolysaccharide (LPS, 1.2 μg/ml) or excitotoxin kainic acid (KA, 150 μM) for 2 days. The medium was collected for assay of released nitrate/nitrite and the cells were harvested for immunohistochemistry and western blot analysis.

After paraformaldehyde fixation and triton X-100 permeabilization, cells were incubated with primary antibody anti-IL-10 (Chemicon) overnight (4° C.) and subsequently incubated with Donkey anti-goat 488 (Alexa) or Donkey anti-mouse cy3 (Jackson Lab) at room temperature for 90 mins. According to the results (data not shown), LPS or KA treatment induced IL-10 expression in the spinal cord cultures.

Cells were also processed for western blot analysis for inducible nitric oxide synthase (iNOS) and cyclooxygenase-2 (COX-2) expression. Briefly, equal amounts of cell lysate proteins were loaded and separated on SDS-PAGE gels. Electrophoresis was performed according to standard procedures. After electrophoresis, gels were transferred onto PVDF membranes (Millipore, USA) and incubated overnight at 4° C. with antibodies against iNOS (BD transduction, USA) or COX-2 (Cayman). Blots were incubated with a donkey anti-rabbit IgG HRP (horseradish peroxidase)-conjugated secondary antibody (Santa Cruz) or a goat anti-mouse IgG HRP-conjugated secondary antibody (Santa Cruz) for 1 h, and HRP detection was performed using SuperSignal Chemiluminescent Substrate (Pierce, USA).

The production of NO was assayed as accumulation of nitrite in medium using colorimetric reaction with Griess reagent. Briefly, after 2 days of LPS treatment, the culture supernatants (150 μl) were collected and mixed with 50 μl of Griess reagent containing 1% sulfanilaminde/0.1% naphthyl ethylene diamine dihydrochloride/2% phosphoric acid and incubated at room temperature for 10 mins. The absorbance was measured at 540 nm. Sodium nitrite ($NaNO_2$) was used as the standard to calculate nitrogen dioxide (NO2).

As shown in FIGS. 1(A) and (B), LPS induced increase of COX-2 and iNOS expression, the number of iNOS-positive cells, and release of nitric oxide (NO) as shown by nitrate/nitrite level. Silymarin effectively reduced LPS or KA stimulation. Silybin significantly reduced LPS-induced NO release.

Example 3

Silymarin and Silybin Inhibits Cell Proliferation in Mixed Glial Cultures

The proliferative activity of mixed glial cultures was investigated by treating cells with 5-bromo-2-deoxyuridine (BrdU), a thymidine analog incorporated into genetic material during the S phase of mitotic division.

Silymarin or silybin (20–80 μM) was added to subconfluent glial cells for 2 days. Two hours before cell fixation, 5-bromo-2-deoxyuridine (BrdU, 10 μM), which could be taken up by proliferative cells, was added to cultured cells. After being fixed with 4% paraformaldhyde (30 mins, room temperature), cells were treated with 2 M HCl (10 min, at 37° C.) to denature their DNA. Cells were then repeatedly washed with PBS until the pH reached 6.5 or above. Cells were further double-treated with mouse anti-BrdU (1:100, Chemicon, Temecula, Calif.) and rabbit anti-GFAP (1:300, Chemicon) antibodies (4° C., overnight), followed by incubation with FITC- and rhodamine-conjugated secondary antibodies (room temperature, 90 mins). Seven random fields were captured in each well, and BrdU-incorporated cells were counted. The ratio of BrdU/total cells was calculated.

Figure 2:
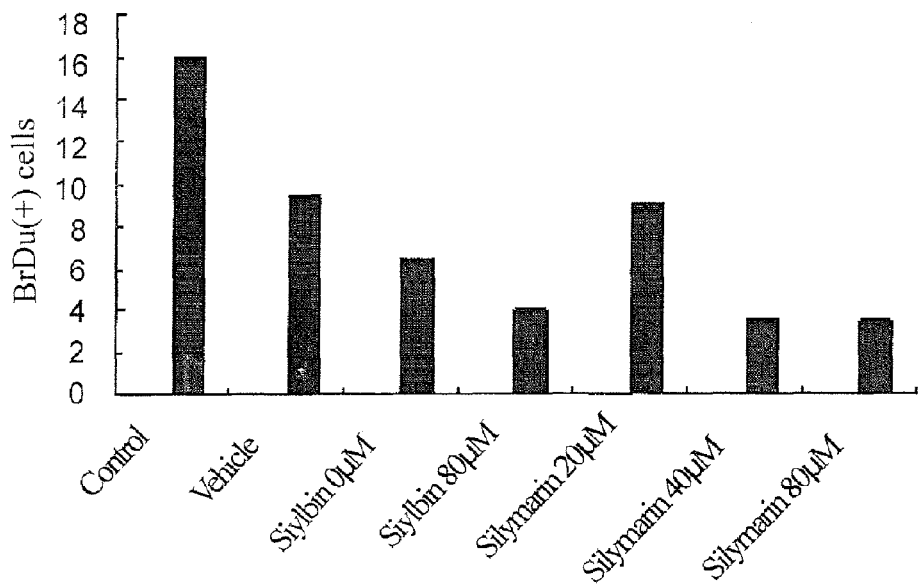
FIG. 2 shows the effect of silymarin and silybin on cell proliferation and on $H_2O_2$-induced free radical formation in mixed glial cultures wherein (A) shows the number of BrdU-positive cells per 1.5 mm$^2$ in each treatment group; and (B) shows effective inhibition of $H_2O_2$-induced free radical formation (ROS) by silymarin (80 µM) and silybin (80 µM).
Figure 2:
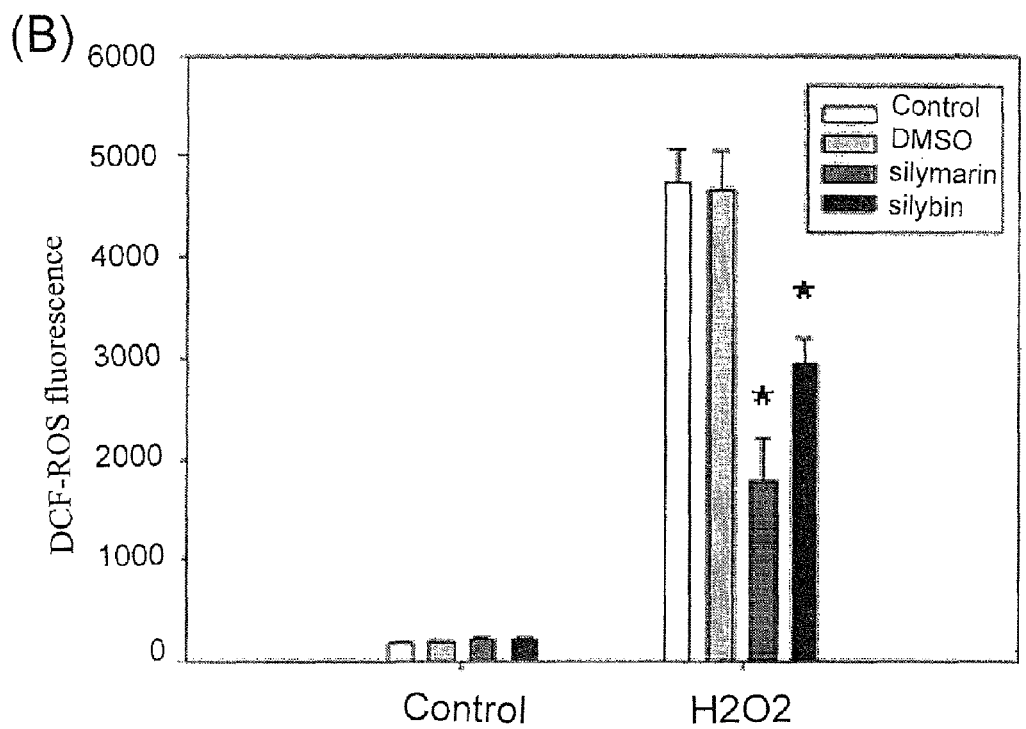

As shown in FIG. 2(A), silymarin and silybin both effectively reduced glial proliferation (indexed by ratio of BrdU (+)/GFAP(+)).

Example 4

Silymarin and Silybin Reduce Toxin-Induced Free Radical Formation in Spinal Cord Astroglial, Microglial and Neuronal-Glial Cultures and Cortical Neuronal-Glial Cultures Antioxidant activity is an important mechanism of action of neuroprotective agents, as free radical damage plays a key role in the neurotoxic effect of various substances as well as in the pathogenesis of such processes as inflammation, ischaemia and reperfusion, atherosclerosis and aging. Free radical levels (oxidative stress) can be induced in cells by challenging with $H_2O_2$ or tert-butyl hydroperoxide (t-BOOH) (see "control" in FIG. 3(C), FIG. 4(A-B) and FIG. 5(A-C)).

In the present example, oxidative stress was induced by treating mixed glial, microglial or mixed neuronal-glial cultures with various free radical generators, and the antioxidant activity of silymarin and silybin was examined by a DCF assay modified for use with a fluorescent microplate reader. The formation of intracellular reactive oxygen species (ROS) is detected by nonfluorescent 2',7'-dichlorodihydrofluorescein diacetate (DCF-DA), a sensitive and widely used probe for the detection of intracellular oxidant production. DCF-DA freely enters the cell and becomes modified by intra cellular esterases into the hydrophilic (and hence "trapped"), nonfluorescent reporter molecule DCF. Oxidation of DCF creates the highly fluorescent DCF, which can be detected by flow cytometry or other fluorescence detection methods.

For the DCF assay, cultures were firstly loaded with 40 μM DCF-DA (Molecular Probe D-399; Invitrogen, Carlsbad, Calif.) in serum-free medium (DMEM+N2) for 1 hr. The medium was then replaced with growth medium containing toxins, including $H_2O_2$ (1 mM for neurons; 3 mM for non-neuronal cells) and t-BOOH (0.75 mM) for 2 hrs. Doses (ranging from 20 to 160 μM) of silymarin or silybin was added to the cultures within 10 mins after the toxin treatment started. The resulted fluorescent DCF levels were measured by a fluorescence plate reader at the excitation/emission of 485 nm/538 nm.

Figure 3:
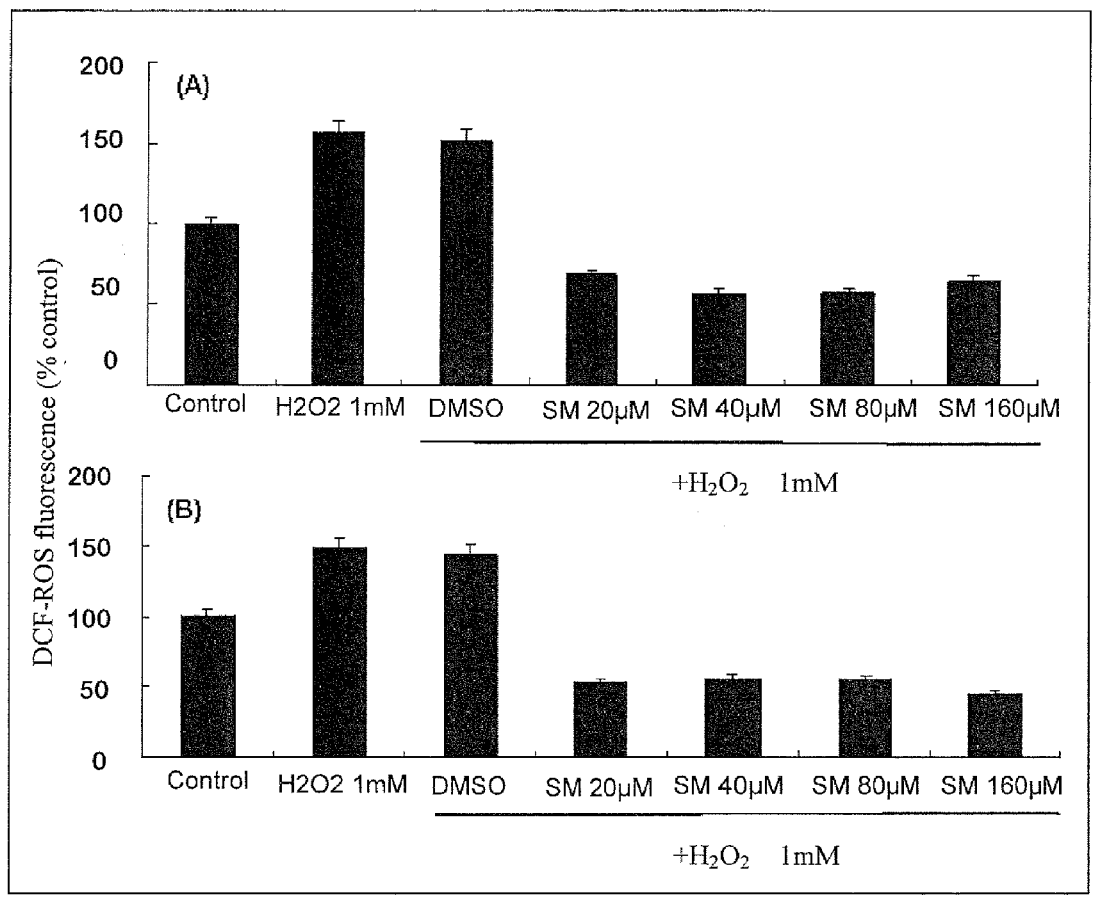
FIG. 3 shows the dose-response protective effect of silymarin on $H_2O_2$-induced free radical formation in neuronal-glial cultures prepared from (A) spinal cord or (B) cortex.
Figure 4:
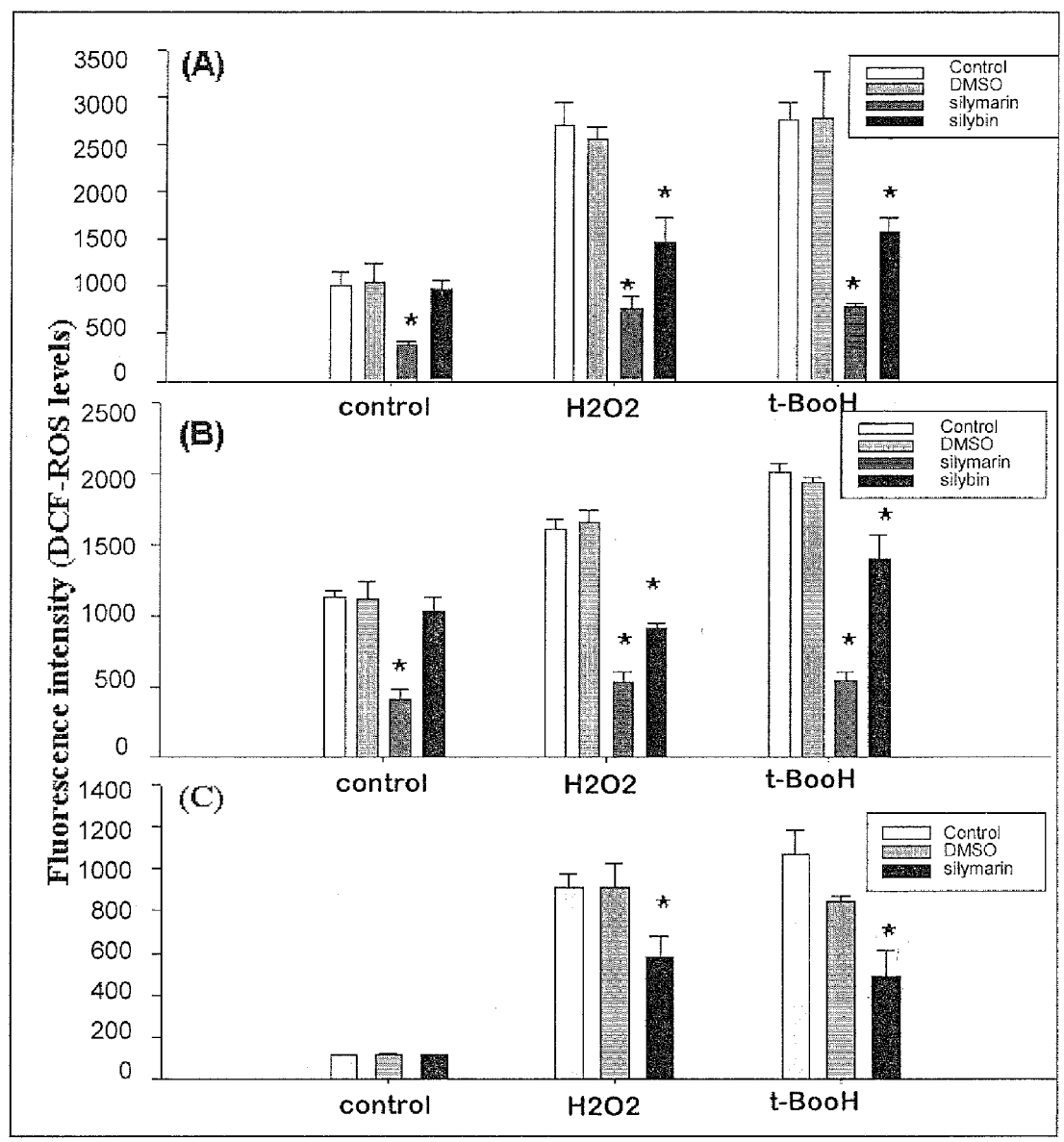
FIG. 4(A) shows the effect of silymarin (80 µM) and silybin (80 µM) on $H_2O_2$- or t-BOOH-induced free radical formation in spinal cord neuronal-glial cultures.
FIG. 4(B) shows the effect of silymarin (80 µM) and silybin (80 µM) on $H_2O_2$- or t-BOOH-induced free radical formation in cortical neuronal-glial cultures.
FIG. 4(C) shows the effect of silymarin (80 µM) on $H_2O_2$- or t-BOOH-induced free radical formation in microglial cultures. (*P<0.05 compared to respective DMSO group)

As shown in FIG. 2(B), FIGS. 3 (A) and (B), and FIG. 4(A) to (C), both silymarin and silybin are strong antioxidants, because they significantly reduced H2O2-or t-BOOH-induced-free radical formation in all cultures tested, including spinal cord mixed glial cultures (FIG. 2(B)), spinal cord mixed neuronal-glial cultures (FIG. 3(A); FIG. 4(A)), cortical mixed neuronal-glial cultures (FIG. 3(B), FIG. 4(B)) and spinal cord microglial cultures (FIG. 4(C)). Importantly, silymarin, ranging from 20 μM to 160 μM, is effective in reducing $H_2O_2$-induced free radical in spinal or cortical mixed neuronglial cultures (FIGS. 3 (A) and (B)).

The degree of MTT (3-(4,5-Dimethylthiazol-2yl)-2,5-diphenyl tetrazolium) reduction is used for measuring cell viability or for determining the metabolic activity of living cells. MTT is reduced by mitochondrial enzymes of viable cells to a blue formazan product which is proportional to the integrity of metabolic functions (Edmondson et al., *J. Tiss. Cult. Meth.* 11 (1998): 15-17). For the MTT assay, the cultures were treated with toxins and silymarin or silybin for 2 hrs as described above. After treatment, the culture medium was removed from the well and replaced by MTT at 0.5 mg/mL in PBS supplemented with glucose (5 mM). After 2 hrs of incubation at 37° C., this solution was removed and the blue formazan crystals were solubilized in acidified isopropanol. The optical density of the resulted solution was measured by a spectrophotometer at 570 nm.

Figure 5:
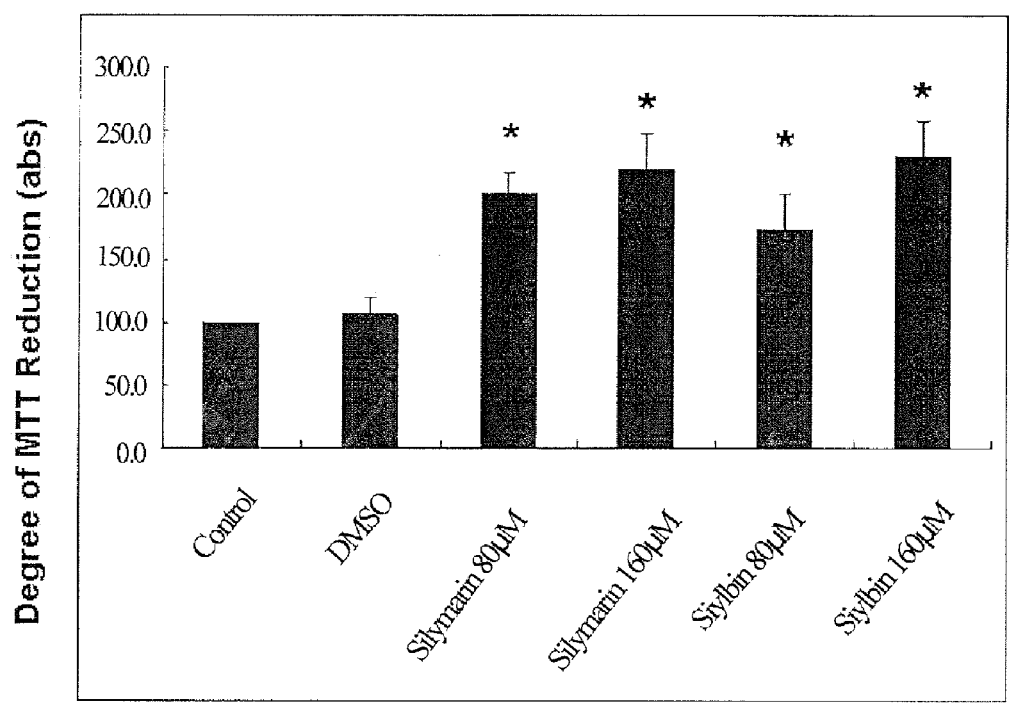
FIG. 5 shows the results of silymarin and silybin in the MTT assay.

As shown in FIG. 5, silymarin and silybin strongly enhanced MTT reduction. The MTT reduction assay depends on the ability of metabolically active cells to reduce the MTT tetrazolium salt to formazan. Reduced pyridine nucleotide cofactor, NADH, is responsible for most MTT reduction. This indicates a strong antioxidative property of silymarin and silybin.

Example 5

Effect of Intrathecal Administration of Silymarin on Contusive SCI

Figure 6:
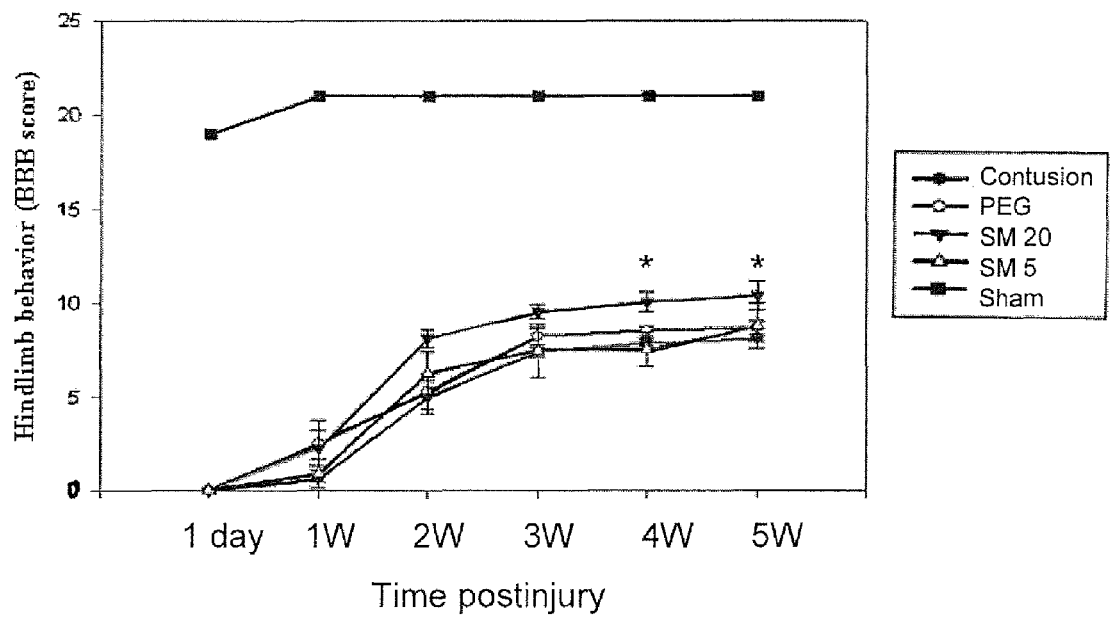
FIG. 6 shows the effect of intrathecally-administered silymarin in contusive SCI rats demonstrated by restoration of their hindlimb function (SM20=20 µg/µl of silymarin in 50% PEG, 6 µl/rat; SM5=5µg/µl of silymarin in 50% PEG, 6 µl/rat; *P<0.05 by one way ANOVA and Student-Newman-Keuls Method).

Since direct infusion of high concentration of (pure) DMSO may cause neurotoxicity, an alternative safer agent, polyethylene glycol (PEG; MW 2000 Da), was used to dissolve silymarin for intrathecal injection. PEG, a hydrophilic polymer, has been demonstrated to be safe and neuroprotective for acute spinal cord injury. (Shi and Borgens, *J. Neurophysiol.* 81 (1999): 2406-2414; Shi et al., *J. Neurotrauma* 16 (1999): 727-738; Shi and Borgens, *J. Neurocytol.* 29 (2000): 633-644). A solution of PEG (50%) was prepared in saline. Silymarin was then dissolved in PEG solution at a concentration of 5 or 20 mg/ml. Six microliter of PEG with or without silymarin was intrathecally administered to the epicenter of injured spinal cord within 30 mins after eliciting contusive injury. The skins were sutured and the hindlimb function (BBB scale) was monitored second day and weekly after spinal cord injury as described above. As shown in FIG. 6, intrathecal silymarin injection (20 μg/μl) significantly facilitated functional recovery in SCI rats, while PEG, the vehicle for silymarin, is not neuroprotective. At 5 weeks postinjury, rats were anesthetized and perfused intravascularly with 4% paraformaldehyde. The spinal cords were then sagittally sectioned (10 μm-thick)and processed for immunohistochemical staining with anti-neurofilament (for neurons) or anti-ED1 (for activated microglia). According to the results (data not shown), the spinal axons (neurofilament positive) were better preserved and less degree of microglial activation (ED-1) was found in silymarin-treated spinal Traumatic spinal cord injury is devastating and initiates a series of cellular and molecular events that include both primary and secondary injury cascades. Injury to the spinal cord provokes an inflammatory reaction that initially results in further tissue damage. Attenuation of the early inflammatory response to spinal cord injury may therefore limit the extent of tissue injury, and accordingly, the consequent disability. SCI rats with or without intrathecally-administered silymarin were sacrificed at three days postinjury. The injured epicenter of spinal cords was rapidly removed and homogenized in ice-cold extraction buffer (7 M urea, 2 M thiourea, 4% CHAPS, 40 mM Tris buffer (pH7.5) and protease inhibitors (Roche 11836145001)). The Bradford method (Bio-Rad Protein Assay, Bio-Rad Laboratories) was used to measure protein concentrations. Equal amounts of proteins were loaded and separated on 8% SDS-PAGE gels. After transfer, the resulted PVDF membrane was probed with anti-COX-2, anti-ED-1 and anti-actin antibodies. Consistent with the results in FIG. 6, intrathecally-administered silymarin reduced expression of COX-2, a proinflammatory enzyme and inhibited ED-1 (+) microglial infiltration in injured spinal cord at 3 days postinjury.

Figure 7:
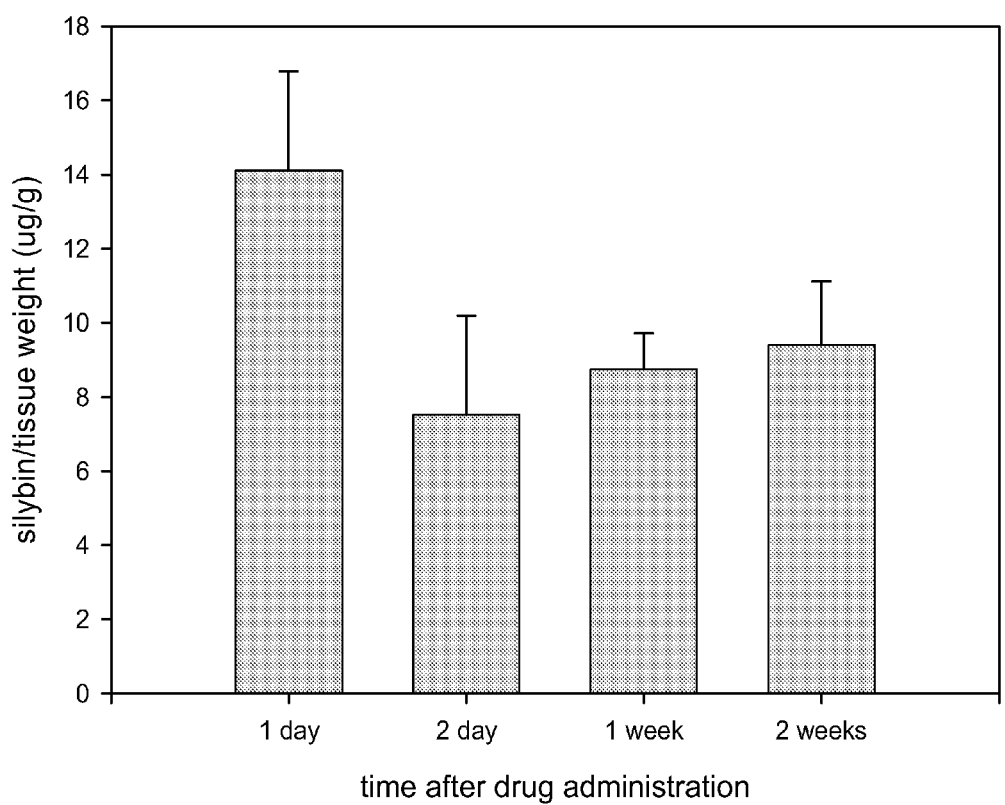
FIG. 7 shows silybin retention in injured spinal cord at various time courses after intrathecal administration of silymarin (120 µg/rat).

Intrathecal silymarin's disposition may be different from that of systemic sc administration. SCI Rats were intrathecally administered with silymarin (120 μg/6 μl/rat). At 1, 2, 7 and 14 days after injury, the spinal cord epicenter was removed and homogenized in 5 volumes of 50 mM Tris-HCl (pH 7.4). Tissue homogenate was further extracted by equal volume of solvent (butanol: methanol, 95:5; v/v). After centrifugation, the resulted organic layer was collected, concentrated and injected directly to the HPLC equipment with UV detection. FIG. 7 shows the time courses of silymarin exposure attained in the spinal cords (pharmacokinetics). Silymarin's disposition is limited in injured spinal epicenter. At 2 weeks post injection, about 8 μg/g tissue of silymarin was still retained. Thus, differences in silymarin's pharmacokinetics may account for the efficient outcome of intrathecal silymarin injection It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for treating spinal cord injury (SCI) comprising intrathecally administering to a subject in need thereof a pharmaceutical composition including an effective amount of silymarin, wherein silymarin is the only active ingredient in the pharmaceutical composition.

2. The method of claim 1, wherein the pharmaceutical composition is administered to an injured neural area.

3. The method of claim 1, wherein the SCI is contusive SCI.

4. The method of claim 3, wherein the pharmaceutical composition is administered to an injured neural area.

* * * * *